United States Patent
Higbie et al.

(10) Patent No.: US 11,039,789 B2
(45) Date of Patent: Jun. 22, 2021

(54) IN-VIVO MAGNETIC DETECTION OF MAGNETIC NANOPARTICLES USING MICRONEEDLES

(71) Applicant: Verily Life Sciences LLC, Mountain View, CA (US)

(72) Inventors: James Michael Higbie, Palo Alto, CA (US); Victor Marcel Acosta, San Francisco, CA (US); Vikram Singh Bajaj, Menlo Park, CA (US); Vasiliki Demas, San Francisco, CA (US); Kimberly Kam, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 261 days.

(21) Appl. No.: 16/378,043

(22) Filed: Apr. 8, 2019

(65) Prior Publication Data

US 2019/0231264 A1  Aug. 1, 2019

Related U.S. Application Data

(63) Continuation of application No. 14/948,693, filed on Nov. 23, 2015, now abandoned.

(51) Int. Cl.
  *A61B 5/05* (2021.01)
  *A61B 5/00* (2006.01)
  *A61B 5/0515* (2021.01)

(52) U.S. Cl.
  CPC ............ *A61B 5/685* (2013.01); *A61B 5/0084* (2013.01); *A61B 5/0515* (2013.01); *A61B 5/6833* (2013.01); *A61B 2562/0223* (2013.01)

(58) Field of Classification Search
  CPC ..... A61B 5/685; A61B 5/0084; A61B 5/0515; A61B 5/6833; A61B 2562/0223
  See application file for complete search history.

(56) References Cited

U.S. PATENT DOCUMENTS

| | | |
|---|---|---|
| 8,361,037 B2 | 1/2013 | Gonnelli |
| 2003/0135167 A1 | 7/2003 | Gonnelli |
| 2004/0056647 A1 | 3/2004 | Stauth et al. |
| 2009/0220932 A1 | 9/2009 | Ingber et al. |
| 2013/0165772 A1 | 6/2013 | Traverso et al. |
| 2013/0210680 A1 | 8/2013 | Derda et al. |

*Primary Examiner* — Mark D Remaly
(74) *Attorney, Agent, or Firm* — McDonnell Boehnen Hulbert & Berghoff LLP (57) ABSTRACT

Systems and methods are described that enable sensing of magnetic fields within skin tissue. Specifically, a system includes one or more microneedles that include a high magnetic permeability material. The system also includes a magnetic sensor communicatively coupled to the microneedle and configured to detect a magnetic field proximate to the microneedle. The system also includes a controller configured to receive information indicative of a magnetic field proximate to a portion of the microneedle. The controller is further configured to determine a presence of at least one magnetic nanoparticle proximate to the portion of the microneedle based on the received information. Alternatively, other embodiments include a microneedle that includes a nanodiamond material configured to detect a local magnetic field. Such embodiments also include a light source configured to cause the nanodiamond material to emit characteristic emission light that may indicate at least a magnitude of the magnetic field.

7 Claims, 8 Drawing Sheets

IN-VIVO MAGNETIC DETECTION OF MAGNETIC NANOPARTICLES USING MICRONEEDLES

CROSS-REFERENCE TO RELATED APPLICATION

This application is a continuation of U.S. patent application Ser. No. 14/948,693, filed Nov. 23, 2015, which is incorporated herein by reference.

BACKGROUND

Microneedle arrays have been developed as an alternative to needle and syringe injections. Such arrays have been used as drug delivery devices, offering the potential of less pain and bleeding at the application site as well as specific penetration depths.

In addition to delivering drug therapies, microneedle arrays may additionally offer new ways to obtain information from embedded or implanted bio-sensors. For example, a plurality of individual microneedle probes may provide a corresponding array of access points to make measurements within tissue.

SUMMARY

In a first aspect, a system is provided. The system includes at least one microneedle configured to be embedded in skin tissue. The at least one microneedle includes a high magnetic permeability material. The system also includes a sensor communicatively coupled to the at least one microneedle. The sensor is configured to detect a magnetic field proximate to the at least one microneedle. The system additionally includes a controller. The controller includes at least one processor and is programmed to carry out operations. The operations include receiving, via the sensor, information indicative of a magnetic field proximate to a portion of the at least one microneedle. The operations also include determining a presence of at least one magnetic nanoparticle proximate to the portion of the at least one microneedle based on the received information.

In a second aspect, a system is provided. The system includes at least one microneedle configured to be embedded in skin tissue. The at least one microneedle includes a sensor. The sensor includes a diamond material. The system also includes a light source optically coupled to the at least one microneedle. The light source is configured to illuminate the sensor. The system additionally includes a controller that includes at least one processor. The controller is programmed to carry out operations. The operations include causing the light source to illuminate the sensor and receiving, via the sensor, information indicative of a magnetic field proximate to the sensor. The operations yet further include determining a presence of at least one magnetic nanoparticle proximate to the sensor based on the received information.

In a third aspect, a method is provided. The method includes receiving, via a sensor coupled to at least one microneedle, information indicative of a magnetic field proximate to a portion of the at least one microneedle. The at least one microneedle is configured to be embedded in skin tissue. The at least one microneedle includes a high magnetic permeability material. The method includes determining a presence of at least one magnetic nanoparticle proximate to the portion of the at least one microneedle based on the received information.

Other aspects, embodiments, and implementations will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where an application of the microneedles disclosed herein may be desired or useful. The environment may include any living or non-living body or a portion thereof. The environment may include non-human tissues. Moreover, while the present disclosure describes embodiments for use in vivo, one of skill in the art will also recognize that in vitro applications are possible as well.

Overview

Labeling of biological molecules with magnetic nanoparticles is an area of significant recent interest for in vivo diagnosis and monitoring, including early detection of cancerous cells in the bloodstream. In such applications, magnetic nanoparticles may be functionalized to bind to a specific target in the blood, and a high sensitivity magnetic sensor outside the body may be configured to monitor the passage of these particles through a nearby blood vessel. However, due to the small size of the magnetic nanoparticles involved and their depth within the body, small values of magnetic flux density are often present at the sensor location. In other words, the sensing capability of magnetic sensors located outside the skin surface may be limited due to magnetic field fall-off between the sensor and the analyte of interest, a distance which may be several millimeters.

The present disclosure describes systems and methods that include the use of microneedles inserted into skin tissue to enhance the magnetometric detection efficiency of magnetic nanoparticle-labeled biological targets in vivo.

In an embodiment, at least one microneedle may be configured to be embedded in skin tissue, such as a transdermal microneedle array. In an example embodiment, a system may include at least one microneedle that includes a high magnetic permeability material.

Magnetic permeability, $\mu$, is the ability of a particular material to support a magnetic field. Put another way, permeability is the degree of magnetization obtained or induced in the material in response to an applied magnetic field. The units of magnetic permeability are generally expressed as henries per meter (H/m) or newtons per ampere squared (N/A$^2$).

As described herein, the high magnetic permeability material may include a material with a high relative magnetic permeability, $\mu_r$. $\mu_r$ may be indicative of the ratio of the magnetic permeability of the high magnetic permeability material, $\mu$, to the magnetic permeability of free space, $\mu_0$. In an example embodiment, $\mu_r$ of the high magnetic permeability material may be greater than 100. Thus, the high magnetic permeability material may have a magnetic permeability that is at least 100 times that of free space. The high magnetic permeability material may include mu-metal, permalloy, iron, or other materials.

A sensor (e.g. a magnetic sensor) may be communicatively coupled to the at least one microneedle. In such a scenario, the sensor may be configured to detect a magnetic field proximate to the at least one microneedle. The sensor may be a Hall effect sensor, a micro-electromechanical system (MEMS) magnetic sensor, or a variable reluctance sensor, among other examples. In an example embodiment, the sensor may be incorporated into the at least one microneedle. Additionally or alternatively, the sensor may be located elsewhere, such as at or near the skin surface.

The system may include a controller that includes at least one processor. The controller may be configured to carry out operations. The operations may include receiving, via the sensor, information indicative of a magnetic field proximate to a portion of the at least one microneedle. The operations may also include determining a presence of at least one magnetic nanoparticle proximate to the at least one microneedle based on the received information.

In some embodiments, the system may include a magnetic field source. For example, the magnetic field source may be configured to provide, increase, or otherwise adjust a magnetic field proximate to the at least one microneedle. In such a scenario, the magnetic field source may include an electromagnet or a permanent magnet.

In an example embodiment, the at least one microneedle may include multiple microneedles, such as a microneedle array. In such a scenario, the microneedle array may be incorporated into a transdermal patch. Other form factors are possible.

Embodiments that include high magnetic permeability materials may concentrate, focus, or otherwise modify the magnetic flux so as to enhance a signal from the magnetic sensor. Because the magnetic field of magnetized nanoparticles on a cell is approximately dipolar at distances large compared to the size of the cell/particle complex, the magnetic flux density (B(r)) decreases approximately as the cube of the separation distance.

$$B(r) = \frac{\mu_0}{4\pi}\left(\frac{3r(m \times r)}{r^5} - \frac{m}{r^3}\right),$$

where m is the magnetic moment and r is separation distance from the nanoparticle.

By guiding and concentrating the magnetic flux from near the nanoparticles, where the flux density is much higher than at the surface, order of magnitude enhancements of flux density can be achieved. In some embodiments, the higher magnetic flux densities may be detected by an atomic magnetometer (or another type of magnetic sensor) external to the body. Once guided to the surface, the magnetic flux may be deconcentrated via a magnetic flux guide in order to optimize coupling to the magnetic sensor.

Additionally or alternatively, a system may include at least one microneedle that includes a sensor incorporating a diamond material. Such a microneedle with diamond material may be termed a nano/microdiamond sensor.

In an example embodiment, the diamond material may include a nitrogen vacancy center defect (N-V center). The N-V center includes a nitrogen atom taking the place of a carbon atom next to a vacancy in the diamond lattice structure. Such N-V centers cause the nanodiamond materials to act like "artificial atoms". N-V centers may be formed using ion implantation, among other techniques. In some embodiments, the at least one microneedle may be made substantially or entirely from diamond and the N-V center may be located at or near a tip of the at least one microneedle.

Such nanodiamonds may utilized to non-invasively measure magnetic fields. For example, in response to pump laser light, the nanodiamond may emit light in the red or infrared wavelengths. The intensity and wavelength(s) of the emission light may depend on magnetic fields applied to the nanodiamond. In some example embodiments, the nanodiamonds may be injected into skin tissue, and/or may be present in circulating blood. As such, nanodiamonds may be deployed as probes to measure magnetic fields within the body. Furthermore, the nanodiamond sensors may be interrogated and read-out using all-optical (non-contact) techniques.

In some examples, one or more microwave pulses may be applied to the nanodiamond so as to initialize the system and/or to obtain more information about the magnetic field and/or other conditions proximate to the nanodiamond. For example, a pulsed electron paramagnetic resonance (EPR) or electron spin resonance (ESR) technique may be applied to determine a spin-relaxation time ($T_1$) and/or a spin-spin relaxation time ($T_2$). In such a scenario, $T_1$ and $T_2$ may be useful to determine a temperature of the nanodiamond as well as an orientation and magnitude of the local magnetic field.

As described above, the system may include a light source optically coupled to the nano/microdiamond sensor. The light source may be optically coupled to the sensor via an optical fiber. Alternatively or additionally, other types of optical couplings are contemplated, such as evanescent coupling.

The light source may be configured to illuminate the sensor. In an example embodiment, the light source may be a laser. Such a light source may be operable to optically pump the nanodiamond material.

The system may further include a light detector. The light detector may detect light emitted from the diamond material in response to the pump light. The light detector may include a charge-coupled device (CCD) focal plane array (FPA) or another type of image sensor.

The system may also include a controller. The controller may be programmed to carry out operations such as causing the light source to illuminate the sensor. Furthermore, the controller may be configured to receive, via the sensor, information indicative of a magnetic field proximate to the sensor. In such a scenario, the controller may determine a presence of at least one magnetic nanoparticle proximate to the sensor based on the received information.

System Examples a. Microneedles with High Magnetic Permeability

Figure 1A:
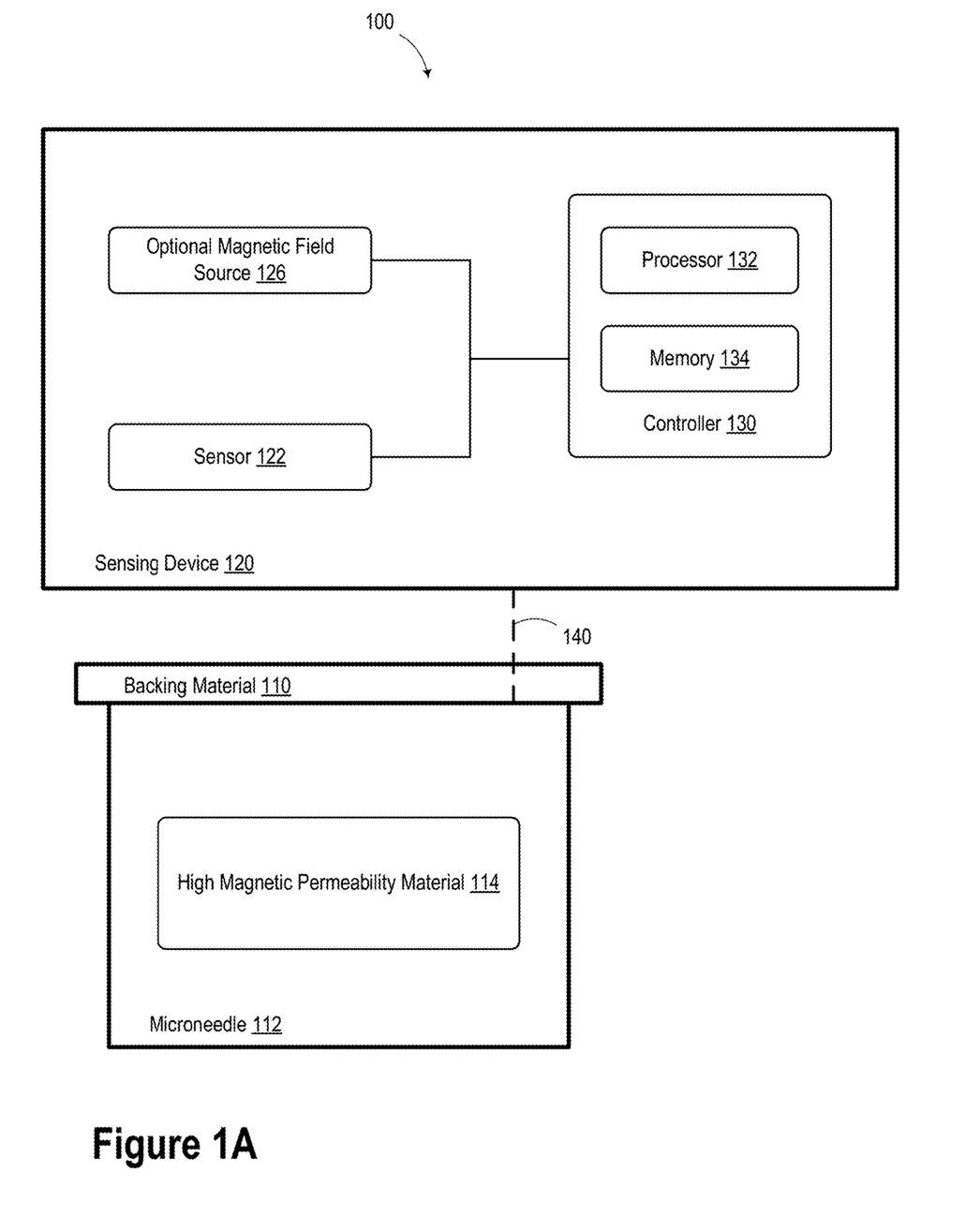
FIG. 1A illustrates a system, according to an example embodiment.
Figure 1B:
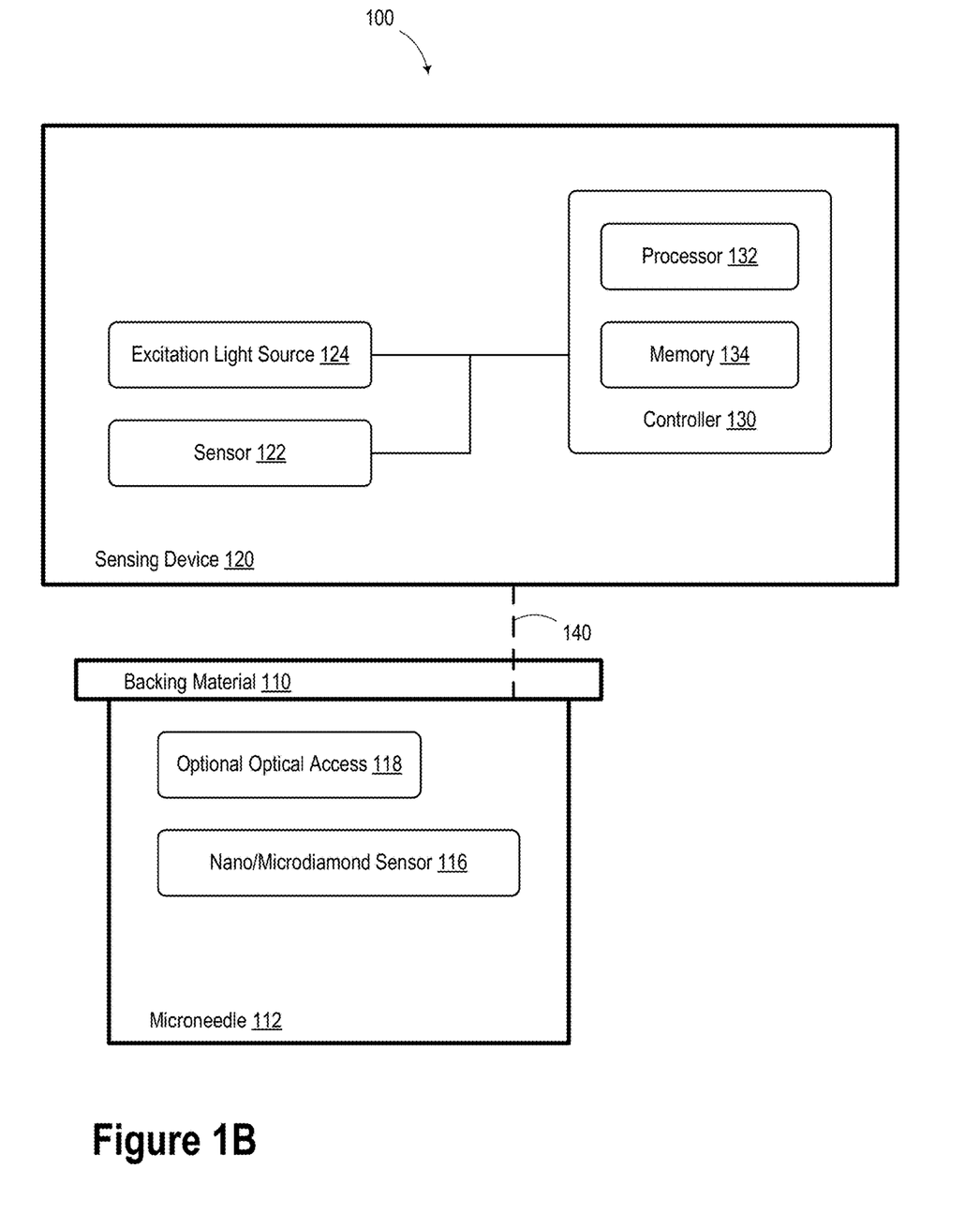
FIG. 1B illustrates a system, according to an example embodiment.

FIGS. 1A and 1B illustrate systems, according to various embodiments. FIG. 1A includes a system 100, which may include one or more microneedles 112 and a backing material 110. The backing material 110 may include a biocompatible material. The backing material 110 may couple to the one or more microneedles 112 so as to form a flexible, biocompatible, transdermal patch having an array of microneedles.

The microneedles 112 may be configured to be embedded in the epidermis and/or the dermis layers of skin tissue. In example embodiments, the one or more microneedles 112 may have a diameter of 100 micrometers, a length between 500-1000 micrometers, and a conical or cylindrical geometry. However, other shapes, sizes, and form factors are possible. The microneedles 112 may include materials such as a hydrogel, a metal, one or more polymers, and/or a plastic. Other materials are possible, as described herein.

The system 100 includes a sensing device 120. The sensing device 120 may include a sensor 122 and a controller 130. The controller 130 may include a processor 132 and a memory 134. Memory 134 could be a non-transitory computer readable medium. The controller 130 may include a mobile device, a laptop computer, or another computing device. The controller 130 may include one or more computers. The one or more computers could be distributed, for example, as part of a cloud server network.

Program instructions may be stored in memory 134 and may be executable by processor 132. Such program instructions may include instructions that carry out or cause the elements of method 300 as illustrated and described in reference to FIG. 3.

The sensor 122 may provide information to the controller 130 indicative of a magnetic field proximate to the one or more microneedles 112. In some embodiments, the information received from the sensor 122 may provide spatially-dependent information about the magnetic field based on a respective spatial position of the one or more microneedles 112.

The sensing device 120 may be optically and/or magnetically coupled to the one or more microneedles 112 via coupling link 140.

In an example embodiment, the one or more microneedles 112 may include a high magnetic permeability material 114. The high magnetic permeability material may include one or more of: mu-metal, nanoperm, iron, permalloy, electrical steel, carbon steel, or nickel. Further materials may include: iron oxide ($Fe_3O_4$), cobalt iron oxide ($CoFe_2O_4$), iron cobalt (FeCo), iron platinum (FePt), etc. Other high magnetic permeability materials may be incorporated into the microneedles 112. For instance, alnico, ferrite, nickel, rare earth materials, and other magnetic materials are possible. Other materials with relative magnetic permeability ($\mu/\mu_o$) above about 100 in the presence of low magnetic field values are contemplated herein.

The high magnetic permeability materials may be incorporated into the microneedles 112 in various positions. In an example embodiment, the microneedle 112 may include a tip portion and a base portion. In such an embodiment, the magnetic material may be disposed at or near the tip portion.

In such a scenario, the coupling link 140 may include a supra-cutaneous magnetic flux guide. The magnetic flux guide may include a permalloy needle and/or wire that may be operable to magnetically couple the one or more microneedles 112 to the sensing device 120. Other types of flux guides are possible. In other embodiments, the coupling link 140 may include magnetic coupling between the microneedles 112 and the sensing device 120 via free-space magnetic field coupling.

The sensor 122 in the sensing device 120 may include a magnetometer configured to measure the absolute and/or relative magnetic field vectors of the coupled magnetic field via the coupling link 140. The sensor 122 may include a superconducting quantum interference device (SQUID), a fluxgate magnetometer (FGM), an inductive coil sensor, a Hall effect sensor, a Faraday force magnetometer, or a magnetoresistive sensor. Other types of devices operable to provide information about the magnetic field near the one or more microneedles 112 are contemplated herein.

In such a scenario, the controller may receive, via the magnetometer (sensor 122), information indicative of the magnetic field proximate to at least a portion of the at least one microneedle 112. Based on the received information, the controller may be configured to determine a presence of at least one magnetic nanoparticle. That is, the presence of the magnetic nanoparticle may be determined to be proximate to the portion of the microneedle 112.

The determination of the presence of the magnetic nanoparticle may be performed in various ways. For example, in the case that the magnetic nanoparticle couples to a tip portion of microneedle 112, a characteristic magnetic field may be measured via the sensor 122. The characteristic magnetic field may include sensing a magnetic field with a field magnitude within a predetermined range. Other characteristic magnetic fields are possible. For example, in the case that the magnetic nanoparticle is circulating in blood, the characteristic magnetic field may include sensing a characteristic rise and fall of a magnetic field magnitude as a magnetic nanoparticle passes near the tip portion of the microneedle 112 and then moves away.

In some embodiments, a number and/or a concentration of magnetic nanoparticles may be determined by counting a number of characteristic magnetic field rise/fall events and/or counting the frequency of such events. Furthermore, gradiometric magnetic imaging with micron-scale resolution may be achieved over centimeter-scale fields of view.

The sensing device 120 may optionally include a magnetic field source 126. The magnetic field source 126 may include a permanent magnet or an electromagnet. For example, the magnetic field source 126 may include ferromagnetic or ferromagnetic materials (e.g. cobalt, iron, iron oxide, nickel, manganese antimonide (MnSb), manganese arsenide (MnAs), etc.). Alternatively or additionally, the magnetic field source 126 may include an electromagnet, which may include a coil of wire around a ferromagnetic core. Other types of electromagnetics are possible.

Embodiments that include a magnetic field source 126 may be operable to deliver, adjust, and/or modify a magnetic field proximate to the one or more microneedles 112. That is, the magnetic field source 126 may be operable to magnetize the microneedles 112. The magnetic field source 126 may apply various magnetic fields to the microneedles 112 by adjusting a current applied to an electromagnetic and/or adjusting a position of the magnetic field source 126 with respect to the microneedles 112.

By applying a magnetic field to the microneedles 112, magnetic nanoparticles (and analytes bound to the magnetic nanoparticles) may be attracted and/or repelled via the magnetic field of the microneedles 112. In such a way, the magnetic nanoparticles may be captured by the microneedles 112. Cell sorting, filtering, and/or organization may be achieved via such an application of magnetic fields via the microneedles 112. That is, cells labeled with magnetic nanoparticles may be captured, filtered, and/or separated from other cells in the tissue.

In yet further embodiments, the magnetic field applied by the microneedles 112 may be used to polarize protons, polarize magnetic nanoparticles (which may in turn be bound to cells or macromolecules), or provide a suitable bias field for a magnetic field sensor located on an adjacent microneedle of the microneedle array.

b. Microneedles with N-V Diamond

FIG. 1B illustrates a system 1 another example embodiment, the one or more microneedles 112 may include at least one nano/microdiamond sensor 116. The nano/microdiamond sensor 116 may include a nanodiamond (N-V diamond) material as described above. As an example, the N-V diamond material may be disposed at or near a tip portion of the one or more microneedles 112. Furthermore, the one or microneedles 112 and/or the backing material 110 may be configured so as to allow optical access 118 to the nano/microdiamond sensor 116.

In such a scenario, the sensing device 120 may be optically coupled to the one or more microneedles 112 via an optical fiber. That is, the coupling link 140 may include an optical fiber. Alternatively or additionally, the optical coupling could be via free-space optical coupling.

The sensing device 120 may include an excitation light source 124. The excitation light source 124 may include a laser. The laser may be operable to provide light at one or more wavelengths so as to excite a relaxation/photoemission event in the nano/microdiamond sensor 116. The excitation light source 124 may be optically coupled via an optical fiber to the nano/microdiamond sensor 116. Additionally or alternatively, the excitation light source 124 may illuminate the skin directly without need for the optical fiber.

The nano/microdiamond sensor 116 may absorb light of a particular wavelength and re-emit light at a longer emission wavelength as emission light. As contemplated herein, nano/microdiamond sensor 116 may be configured to have excitation wavelengths in the green to near infrared wavelengths, but other excitation wavelengths are possible. The nano/microdiamond sensor 116 may have one or more corresponding emission wavelengths in the visible to near-infrared spectrum, but other emission wavelengths are possible.

For example, the excitation light source 124 may be configured to provide light having a wavelength of 532 nm (green). In response to absorbing the excitation light, the nano/microdiamond sensor 116 may emit light having a red and/or infrared wavelength. In the presence of a magnetic field, the emission light may be split into two or more sub-levels, which may occur according to the Zeeman effect.

The Zeeman effect involves the splitting and frequency shifting of a spectral line (e.g. light at the emission wavelength) into several spectral components. As the magnetic field increases, the absolute value of the frequency shift of the emission line and the energy splitting between the spectral components may generally increase. Accordingly, by measuring the emission wavelength and/or the energy splits between spectral components of the emission light, a magnetic field local to the nano/microdiamond sensor 116 may be quantified using a non-invasive technique.

In some example embodiments, the nano/microdiamond sensor 116 may be incorporated into a hydrogel matrix. Alternatively, the nano/microdiamond sensor 116 may be incorporated into a tip portion of the microneedles 112. For example, the microneedle 112 may be formed substantially from diamond and the tip portion could be doped with nitrogen vacancy centers via ion implantation.

Additionally or alternatively, one or more nano/microdiamond sensors 116 may be incorporated into the epidermis, the dermis and/or surrounding tissue, bone, body cavity, blood stream, etc.

As illustrated in FIG. 1B, the sensor 122 may include one or more photodetectors configured to detect the magnitude and spectral components of the emission light emitted by the nano/microdiamond sensor 116. That is, sensor 122 may be a photodetector configured to detect light at least at the emission wavelength of the nano/microdiamond sensor 116. Sensor 122 may include a field of view. The field of view of light sensor 122 may include the skin tissue where the microneedles were deployed and/or determined, at least in part, by an optical fiber coupling the sensor 122 to the nano/microdiamond sensor 116.

In some embodiments, the sensor 122 may be a charge-coupled device (CCD) camera or another type of camera configured to capture images of the field of view so as to identify emission light from a plurality of nano/microdiamond sensors 116.

As described herein, controller 130 may control and/or adjust parameters associated with one or more of the other elements of system 100. For example, the controller 130 may be configured to cause the excitation light source 124 to illuminate the nano/microdiamond sensor 116 via coupling link 140, e.g. an optical fiber. Furthermore, controller 130 may receive from sensor 122 a signal indicative of a magnetic field proximate to the nano/microdiamond sensor 116.

In some embodiments, the microneedles 112 may be coupled to planar photonic waveguide circuits, which may enable more complex functionality (e.g. large area imaging, etc.).

The controller 130 may receive, via sensor 122 (e.g. a photodetector), information indicative of a magnetic field proximate to the nano/microdiamond sensor 116. Again, the received information may include Zeeman-shifted spectra that may include indicia of magnetic field intensity and/or orientation. The information may include other types of indicia about the magnetic field proximate to the nano/microdiamond sensor 116.

Furthermore, the controller 130 may be configured to determine a presence of at least one magnetic nanoparticle proximate to the sensor based on the received information. That is, the controller 130 may be operable to calculate, compute, estimate, or infer the presence of the magnetic nanoparticle based on the received information.

In some embodiments, controller 130 may additionally cause the sensor 122 to capture an image of a field of view that includes at least the nano/microdiamond sensor 116.

In some embodiments, controller 130 may control other aspects of sensor 122. For example, controller 130 may adjust a shutter speed, an integration time, sensitivity, aperture, white balance, sensing wavelength, and/or other aspects of sensor 122.

Controller 130 may also optionally adjust or control various other aspects of system 100. For example, controller 130 may be configured to adjust or control optical components that are configured to focus, direct, steer, adjust, reflect, or attenuate/absorb the light in system 100. For example, controller 130 may control a lens so as to obtain proper focus and/or direction of excitation light. For instance, controller 130 may adjust neutral density filters, spectral filters, shutters, apertures, beam stops, etc. associated with system 100.

c. Microneedle Application Scenarios and Example Microneedles

Figure 2A:
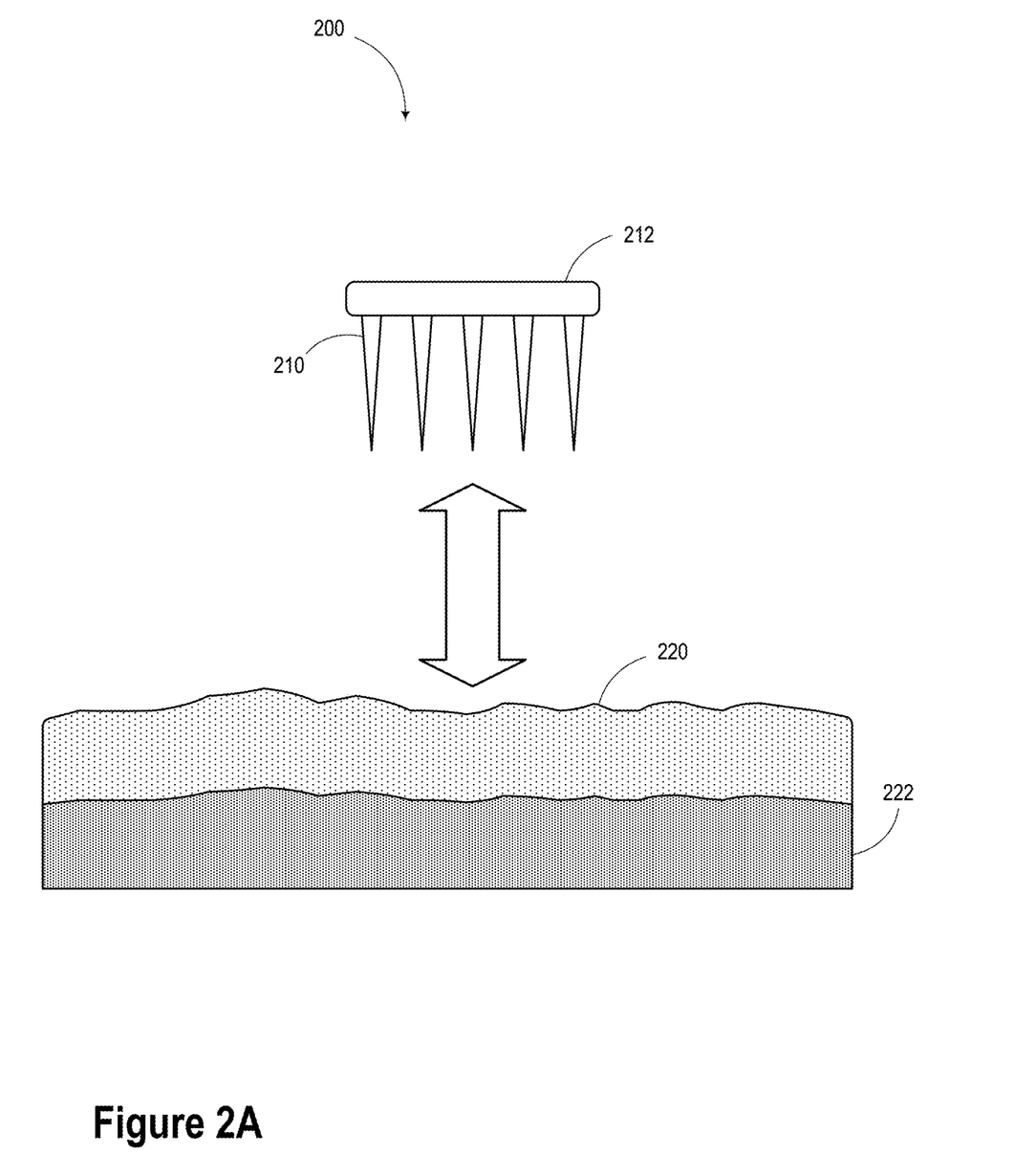
FIG. 2A illustrates a microneedle application scenario, according to an example embodiment.

FIG. 2A illustrates a microneedle application scenario 200, according to an example embodiment. In particular, the scenario 200 may include a plurality of microneedles 210 coupled to a backing material 212. As such, the microneedles 210 and the backing material 212 may be formed into a transdermal patch. The microneedles may be configured to penetrate into the epidermis 220 and dermis 222.

Figure 2B:
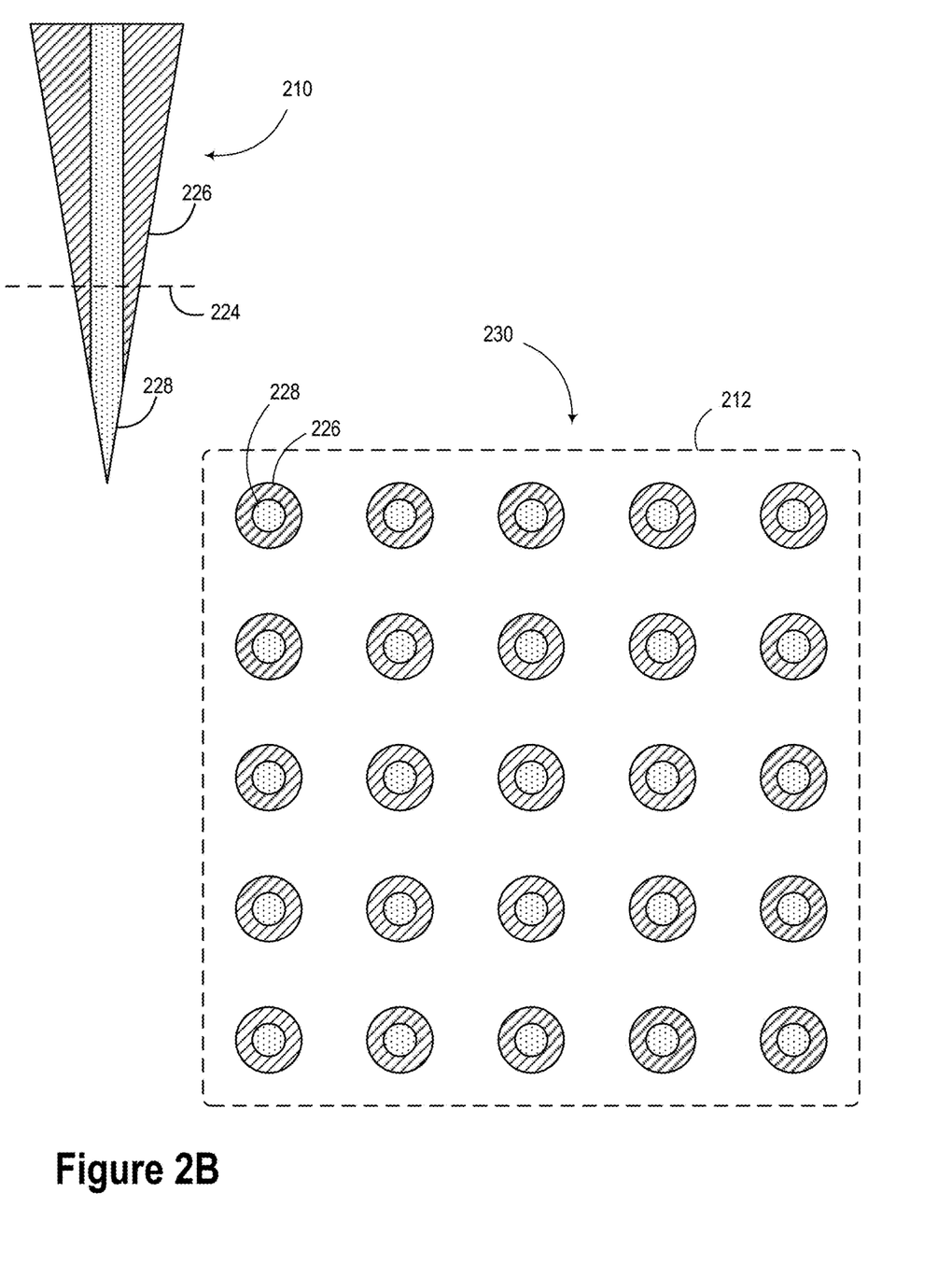
FIG. 2B illustrates a cross-section of a microneedle array, according to example embodiments.

FIG. 2B illustrates a cross section of microneedle 210. Namely, microneedle 210 may include a microneedle core 228 and a magnetic material 226. FIG. 2B also illustrates a cross-section of a microneedle array 230, which may include a view along plane 224. Cross-section 230 includes a view of the backing material 212 as well as an array of microneedles. In an example embodiment, the microneedles may include a magnetic material 226 disposed around a microneedle core 228. The microneedle core 228 may include a hydrogel matrix. For example, the hydrogel matrix may include small molecules configured to provide a therapeutic drug dosage once introduced into skin tissue. Alternatively, the microneedle core 228 may include materials common to optical waveguides and/or optical fibers. Yet further, the microneedle core may optionally or additionally include nano/microdiamond materials, such as those described in reference to FIG. 1B.

Figure 2C:
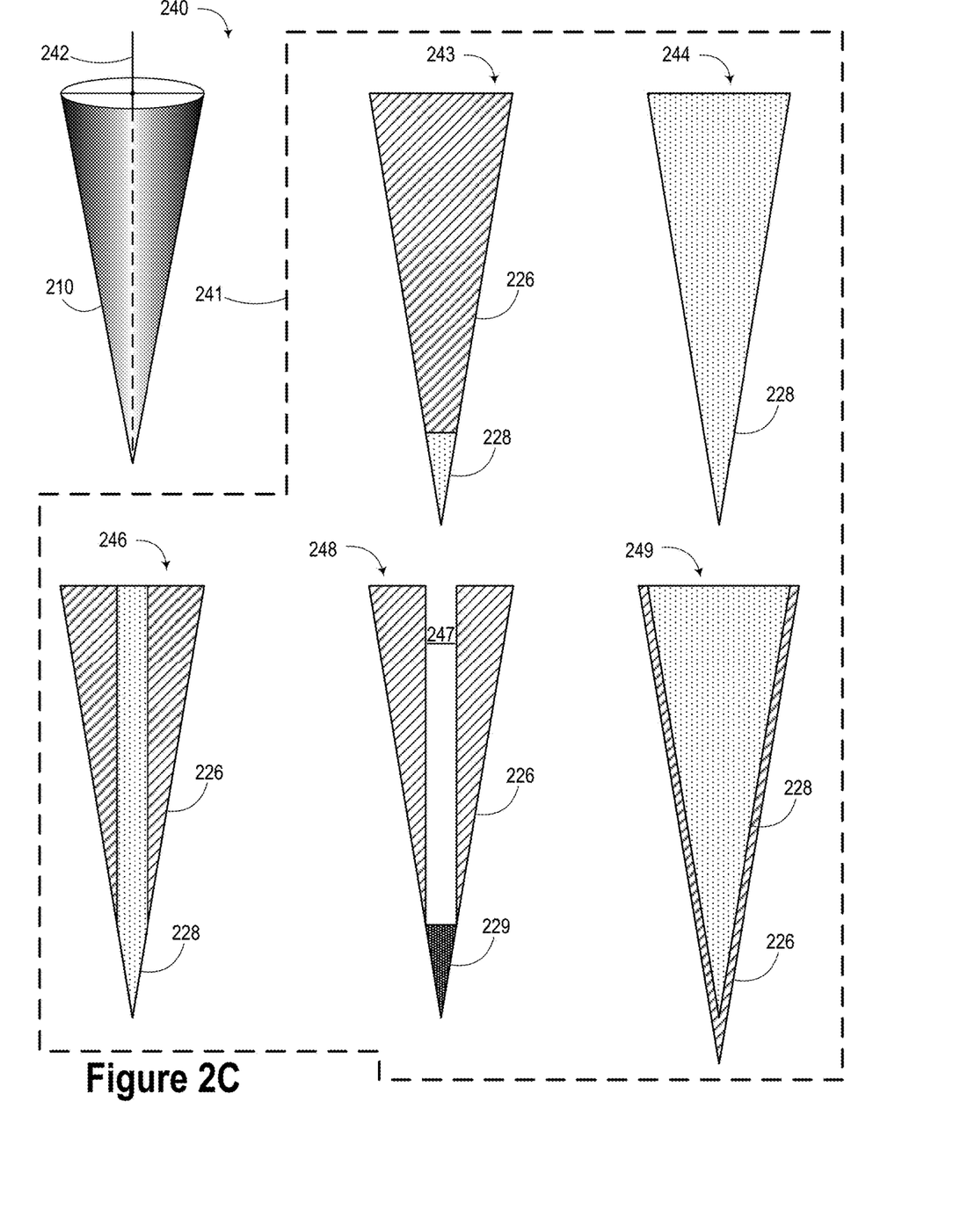
FIG. 2C illustrates several microneedles, according to example embodiments.

FIG. 2C illustrates several microneedles 240, according to example embodiments. Specifically, FIG. 2C illustrates some cross-sections of microneedles contemplated in various embodiments herein. The cross-sections of microneedles are illustrated within area 241 of FIG. 2C. The cross-sections are provided for views along a plane coincident with a central axis 242 of a microneedle 210.

Microneedle 243 includes a high magnetic permeability material 228 incorporated into a tip portion of microneedle 243. In an example embodiment, a base portion 226 of the microneedle 243 may include a hydrogel material.

Microneedle 244 may be completely or substantially formed from high magnetic permeability material 228.

Microneedle 246 may include a core portion made of high magnetic permeability material 228 and a surrounding portion made from a different material, e.g. hydrogel.

Microneedle 248 may include a nano/microdiamond material 229 at or near a tip portion of the microneedle 248. The body of microneedle 248 may be formed from a different material. The body of microneedle 248 may include optical access 247 to the nano/microdiamond material 229.

Microneedle 249 may include a high magnetic permeability material 228. Furthermore, the microneedle 249 may be coated a different material 226. The different material 226 may include a biocompatible material, such as titanium, parylene, or polyethylene.

Although FIG. 2C illustrates certain example configurations of microneedles and corresponding high magnetic permeability material and/or nano/microdiamond material, it is to be understood that other configurations are possible and contemplated herein.

Figure 2D:
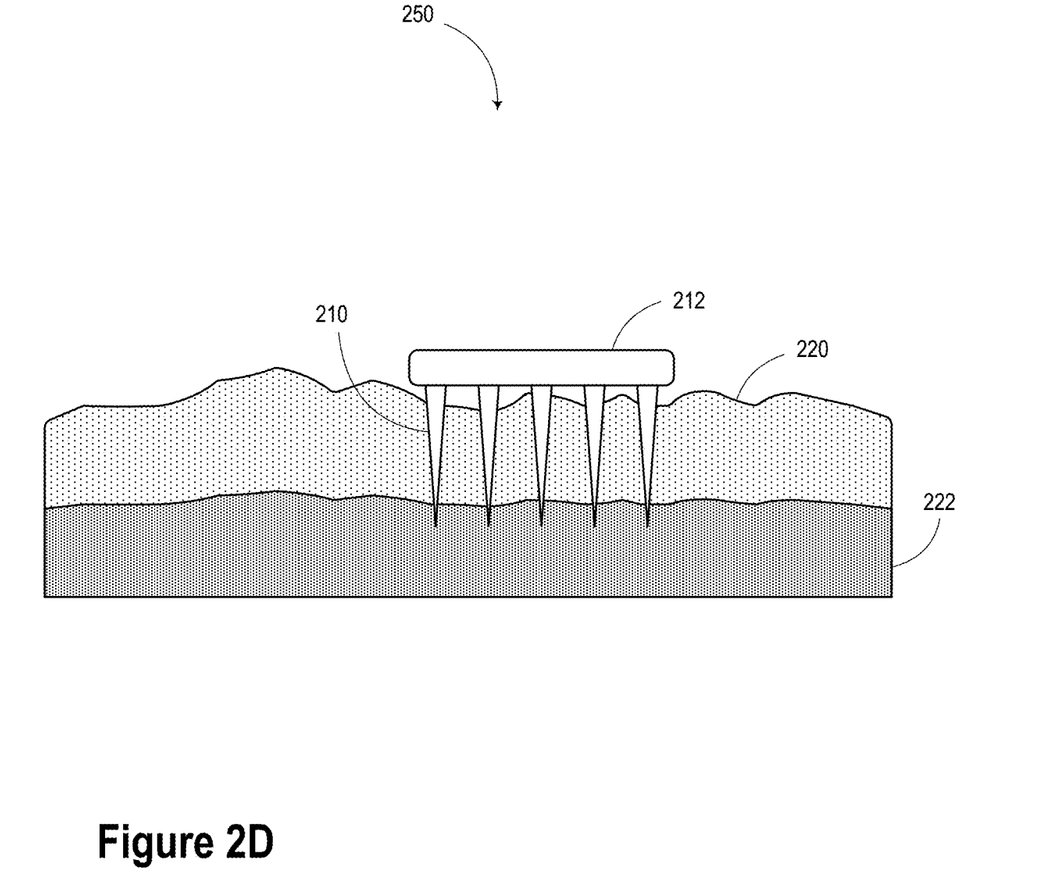
FIG. 2D illustrates a microneedle application scenario, according to an example embodiment.

FIG. 2D illustrates a microneedle application scenario 250, according to an example embodiment. In scenario 250, the backing material 212 and microneedles 210 are applied together so as to penetrate the skin tissue (epidermis 220 and dermis 222). Namely, the application of pressure on the backing material 212 and/or microneedles 210 may push the microneedles 210 through the epidermis layer 220 and into the dermis layer 222, to result in the configuration of embedded microneedles 210 shown in FIG. 2D. As shown, the embedded microneedles 210 extend through the epidermis layer 220 and into the dermis layer 222, such that at least a tip portion of the microneedles 210 is in contact with the dermis layer 222. Further, the base portions of the microneedles 210 may be attached to the backing material 212 outside of the skin tissue.

Figure 2E:
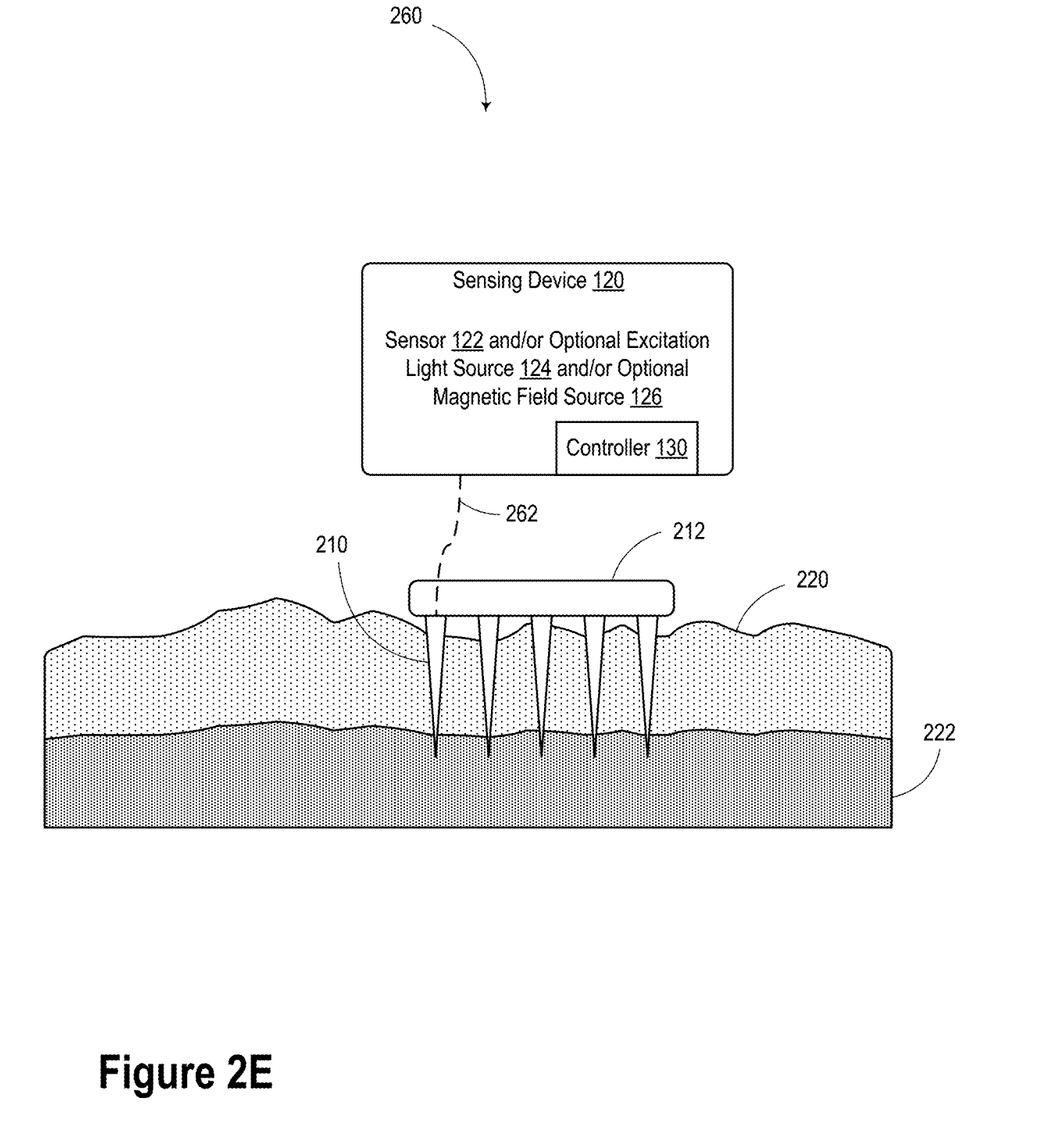
FIG. 2E illustrates a microneedle application scenario, according to an example embodiment.

FIG. 2E illustrates a microneedle application scenario 260, according to an example embodiment. Scenario 260 may include a sensing device 120, as illustrated and described in reference to FIGS. 1A and 1B. The sensing device 120 may include a controller 130, a sensor 122, an excitation light source 124 and/or a magnetic field source 126.

The sensing device 120 may be optically or magnetically coupled to the microneedles 210 via coupling link 262. The coupling link 262 may include an optical fiber, a magnetic flux guide, or a free space link.

The scenario 260 also includes microneedles 210 and a backing material 212. As described with respect to FIG. 2D, the microneedles 210 may penetrate into the skin tissue, such as the epidermis 220 and dermis 222. The sensing device 120 may be optically and/or magnetically coupled to microneedles 210 via an optical fiber and/or magnetic flux guide. Additionally or alternatively, the sensing device 120 may be optically and/or magnetically coupled to the microneedles 210 via free-space field coupling.

Method Examples

Figure 3:
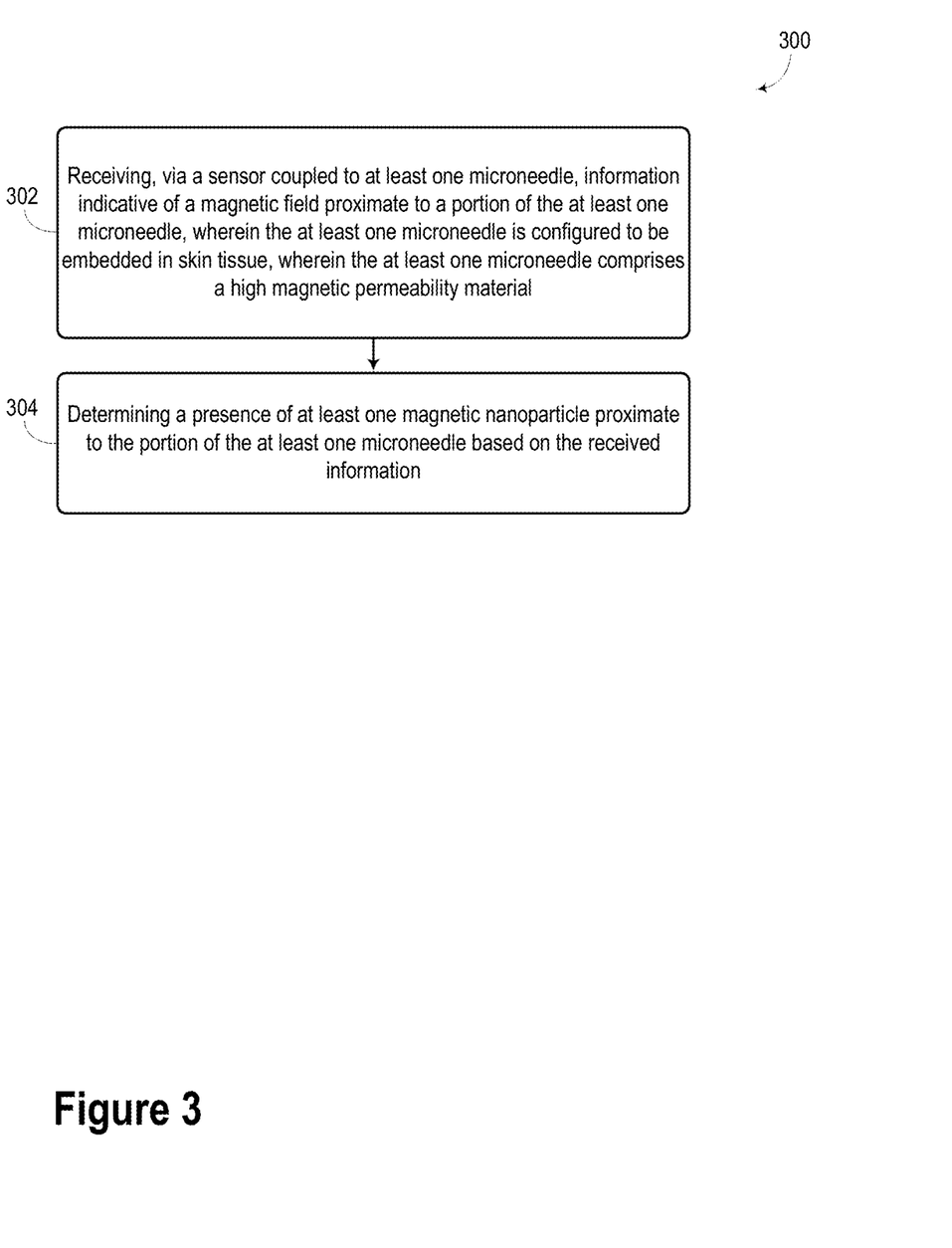
FIG. 3 illustrates a method, according to an example embodiment.

FIG. 3 illustrates a method 300, according to an embodiment. The method 300 includes blocks that may be carried out in any order. Furthermore, various blocks may be added to or subtracted from method 300 within the intended scope of this disclosure. The method 300 may correspond to steps that may be carried out using any or all of the systems illustrated and described in reference to FIG. 1A and FIGS. 2A-2E.

Block 302 includes receiving, via a sensor coupled to at least one microneedle, information indicative of a magnetic field proximate to a portion of the at least one microneedle, wherein the at least one microneedle is configured to be embedded in skin tissue, wherein the at least one microneedle comprises a high magnetic permeability material. The sensor may be sensor 122 as illustrated and described in reference to FIG. 1A. The at least one microneedle may be microneedles 112 and 210 as illustrated and described in reference to FIGS. 1A and 2A-2E.

As described herein, the at least one microneedle may include a plurality of microneedles. The plurality of microneedles may be coupled a transdermal patch. That is, the plurality of microneedles may be coupled to a backing material configured to adhere to an exterior portion of skin. Other arrangements or form factors involving the at least one microneedle are possible.

The high magnetic permeability material may include one of, or any combination of, the high magnetic permeability materials described herein. In an example embodiment, the high magnetic permeability material may include at least one of: mu-metal, permalloy, electrical steel, iron, cobalt-iron, Metglas, ferrite, carbon steel, or nickel. Furthermore, the high magnetic permeability material may have a relative magnetic permeability of at least 100.

In an example embodiment, the sensor may include a magnetic field sensor, such as a Hall effect sensor. Other types of sensors configured to detect a magnetic field are contemplated.

Block 304 includes determining a presence of at least one magnetic nanoparticle proximate to the portion of the at least one microneedle based on the received information. As described herein, determining the presence of the magnetic nanoparticle may include sensing a characteristic magnetic field via controller 130 and sensor 122 as described in reference to FIGS. 1A and 2E.

In an example embodiment, the at least one magnetic nanoparticle may be in interstitial fluid in the dermis or in a blood vessel near the dermis. Alternatively or additionally, the at least one magnetic nanoparticle may be in another blood vessel (e.g. a capillary) proximate to the at least one microneedle.

In some embodiments, a magnetic field source may be provided. The magnetic field source may be configured to adjust the magnetic field proximate to the portion of the at least one microneedle. In such a scenario, the magnetic field source may include an electromagnet and/or a permanent magnet.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:

1. A system, comprising:
    at least one microneedle configured to be embedded in skin tissue, wherein the at least one microneedle comprises a high magnetic permeability material;
    a sensor communicatively coupled to the at least one microneedle, wherein the sensor is configured to detect a magnetic field proximate to the at least one microneedle; and
    a controller comprising at least one processor and programmed to carry out operations, the operations comprising:
        receiving, via the sensor, information indicative of a magnetic field proximate to a portion of the at least one microneedle;
        determining that the information indicative of the magnetic field is characteristic of one or more magnetic nanoparticles being proximate to the portion of the at least one microneedle; and
        responsive to determining that the information indicative of the magnetic field is characteristic of one or more magnetic nanoparticles being proximate to the portion of the at least one microneedle, determining that at least one magnetic nanoparticle is present proximate to the portion of the at least one microneedle.

2. The system of claim 1, wherein the high magnetic permeability material has a relative magnetic permeability μr, wherein μr is a ratio of magnetic permeability of the high magnetic permeability material, μ, to magnetic permeability of free space, μ0, and wherein the relative magnetic permeability of the high magnetic permeability material is at least 100.

3. The system of claim 1, wherein the high magnetic permeability material comprises at least one of: mu-metal, permalloy, electrical steel, iron, cobalt-iron, Metglas, ferrite, carbon steel, or nickel.

4. The system of claim 1, wherein the sensor comprises a magnetic field sensor.

5. The system of claim 1, further comprising a magnetic field source, wherein the magnetic field source is configured to adjust the magnetic field proximate to the portion of the at least one microneedle.

6. The system of claim 5, wherein the magnetic field source comprises at least one of: an electromagnet or a permanent magnet.

7. The system of claim 1, wherein the at least one microneedle comprises a plurality of microneedles, wherein the plurality of microneedles is coupled to a transdermal patch.

* * * * *